(12) United States Patent
Ronnecke et al.

(10) Patent No.: US 9,779,300 B2
(45) Date of Patent: *Oct. 3, 2017

(54) TILED IMAGE BASED SCANNING FOR HEAD POSITION FOR EYE AND GAZE TRACKING

(71) Applicant: SENSOMOTORIC INSTRUMENTS GESELLSCHAFT FUR INNOVATIVE SENSORIK MBH, Berlin (DE)

(72) Inventors: Stefan Ronnecke, Berlin (DE); Thomas Jablonski, Berlin (DE); Christian Villwock, Berlin (DE); Walter Nistico, Berlin (DE)

(73) Assignee: SENSOMOTORIC INSTRUMENTS GESELLSCHAFT FUR INNOVATI, Teltow/Berlin (DE)

( * ) Notice: Subject to any disclaimer, the term of this patent is extended or adjusted under 35 U.S.C. 154(b) by 0 days.
This patent is subject to a terminal disclaimer.

(21) Appl. No.: 15/251,206

(22) Filed: Aug. 30, 2016

(65) Prior Publication Data
US 2017/0076135 A1    Mar. 16, 2017

Related U.S. Application Data

(63) Continuation of application No. 14/428,621, filed as application No. PCT/EP2013/070039 on Sep. 26, 2013, now Pat. No. 9,465,990.

(30) Foreign Application Priority Data

Sep. 27, 2012  (EP) .................................... 12186357
Oct. 24, 2012  (EP) .................................... 12189825

(51) Int. Cl.
G06K 9/00       (2006.01)
A61B 3/113      (2006.01)
(Continued)

(52) U.S. Cl.
CPC ............. *G06K 9/0061* (2013.01); *A61B 3/113* (2013.01); *G06K 9/00362* (2013.01);
(Continued)

(58) Field of Classification Search
CPC ............. G06K 9/0061; G06K 9/00362; G06K 9/00624; G06T 7/004
See application file for complete search history.

(56) References Cited

U.S. PATENT DOCUMENTS 5,859,921 A  *  1/1999  Suzuki ................... G08B 21/06
                                                          382/118
7,362,885 B2 *  4/2008  Hammoud ......... G06K 9/00604
                                                          382/100
(Continued)

FOREIGN PATENT DOCUMENTS

AU        2008229893       5/2009
CN        101282680 A      4/2008
(Continued)

*Primary Examiner* — Nam Pham
(74) *Attorney, Agent, or Firm* — Ronald S. Fernando

(57) ABSTRACT

An eye tracking method comprising: capturing image data by an image sensor; determining a region of interest as a subarea or disconnected subareas of said sensor which is to be read out from said sensor to perform an eye tracking based on the read out image data; wherein said determining said region of interest comprises: a) initially reading out only a part of the area of said sensor; b) searching the image data of said initially read out part for one or more features representing the eye position and/or the head position of a subject to be tracked; c) if said search for one or more features has been successful, determining the region of interest based on the location of the successfully searched one or more features, and d) if said search for one or more features has not been successful, reading out a further part of said sensor to perform a search for one or more features representing the eye position and/or the head position based on said further part.

15 Claims, 7 Drawing Sheets

Scanning for Head Position Using Tile Stitching

(51) Int. Cl.
    *G06T 7/70*           (2017.01)
    *G06K 9/20*           (2006.01)
    *G06T 11/60*         (2006.01)
    *G06T 7/73*           (2017.01)
    *G06T 7/246*         (2017.01)

(52) U.S. Cl.
    CPC ..... *G06K 9/00604* (2013.01); *G06K 9/00624* (2013.01); *G06K 9/2054* (2013.01); *G06T 7/246* (2017.01); *G06T 7/70* (2017.01); *G06T 7/73* (2017.01); *G06T 11/60* (2013.01); *G06T 2207/30201* (2013.01)

(56) References Cited

U.S. PATENT DOCUMENTS

| | | | |
|---|---|---|---|
| 2004/0196433 A1* | 10/2004 | Durnell | G06K 9/00604 351/209 |
| 2010/0045933 A1 | 2/2010 | Eberl et al. | |
| 2010/0303294 A1* | 12/2010 | Zschau | A61B 3/113 382/103 |
| 2012/0169887 A1* | 7/2012 | Zhu | G06T 7/0046 348/207.1 |

FOREIGN PATENT DOCUMENTS

| | | | |
|---|---|---|---|
| SE | WO 2007043954 A1 * | 4/2007 | ........... G06K 9/0061 |
| WO | WO2007043954 | 4/2007 | |
| WO | WO2011049558 | 4/2011 | |

\* cited by examiner

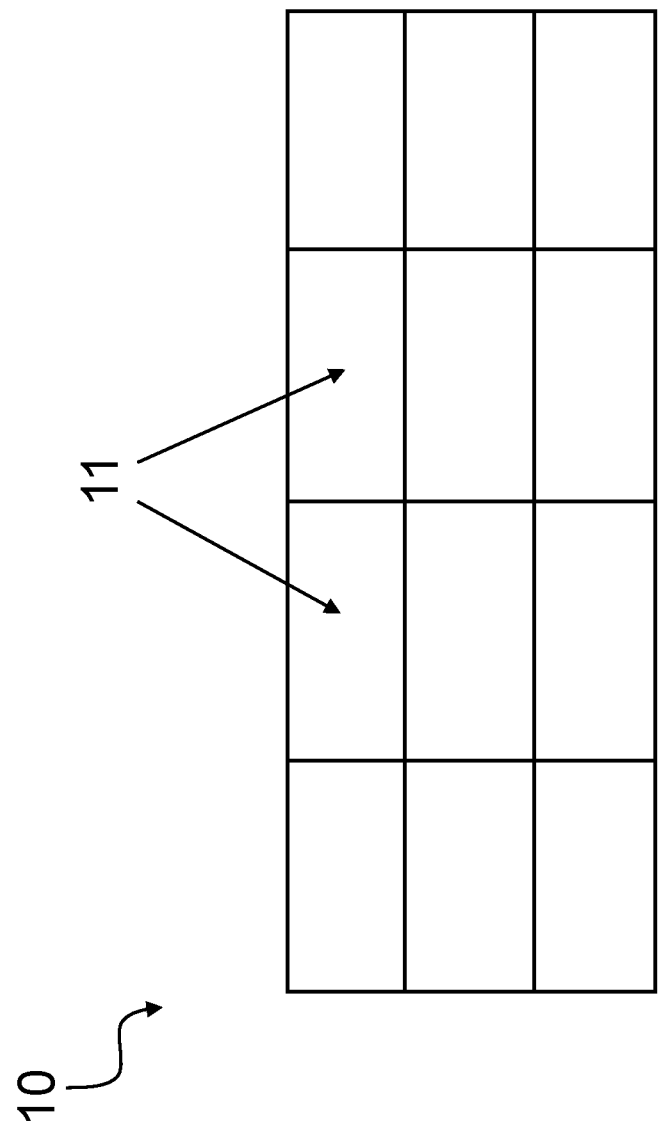
Figure 1: Sensor area 10 split into tiles 11

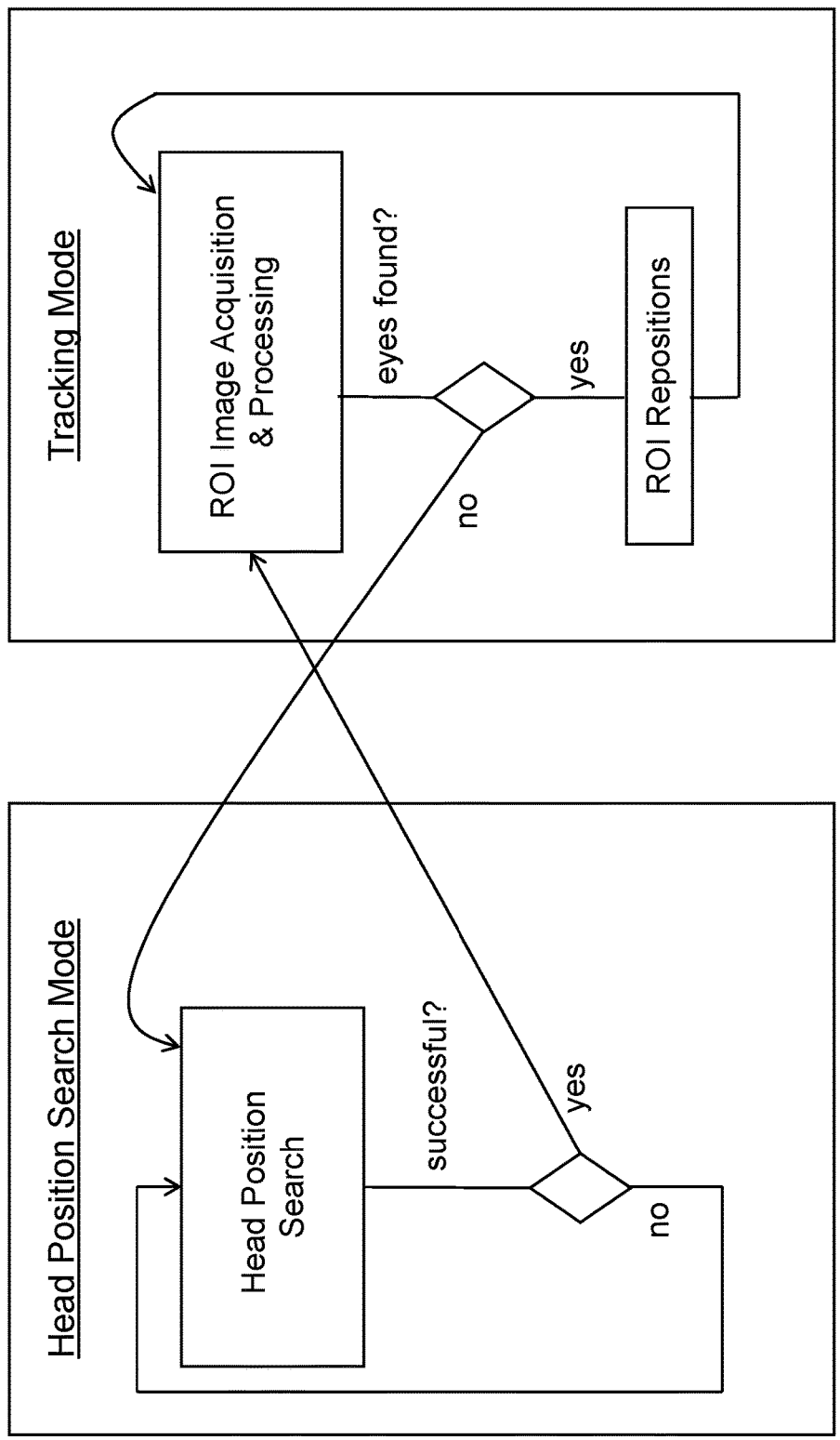
Figure 2: Head Position Search Mode and Tracking Mode

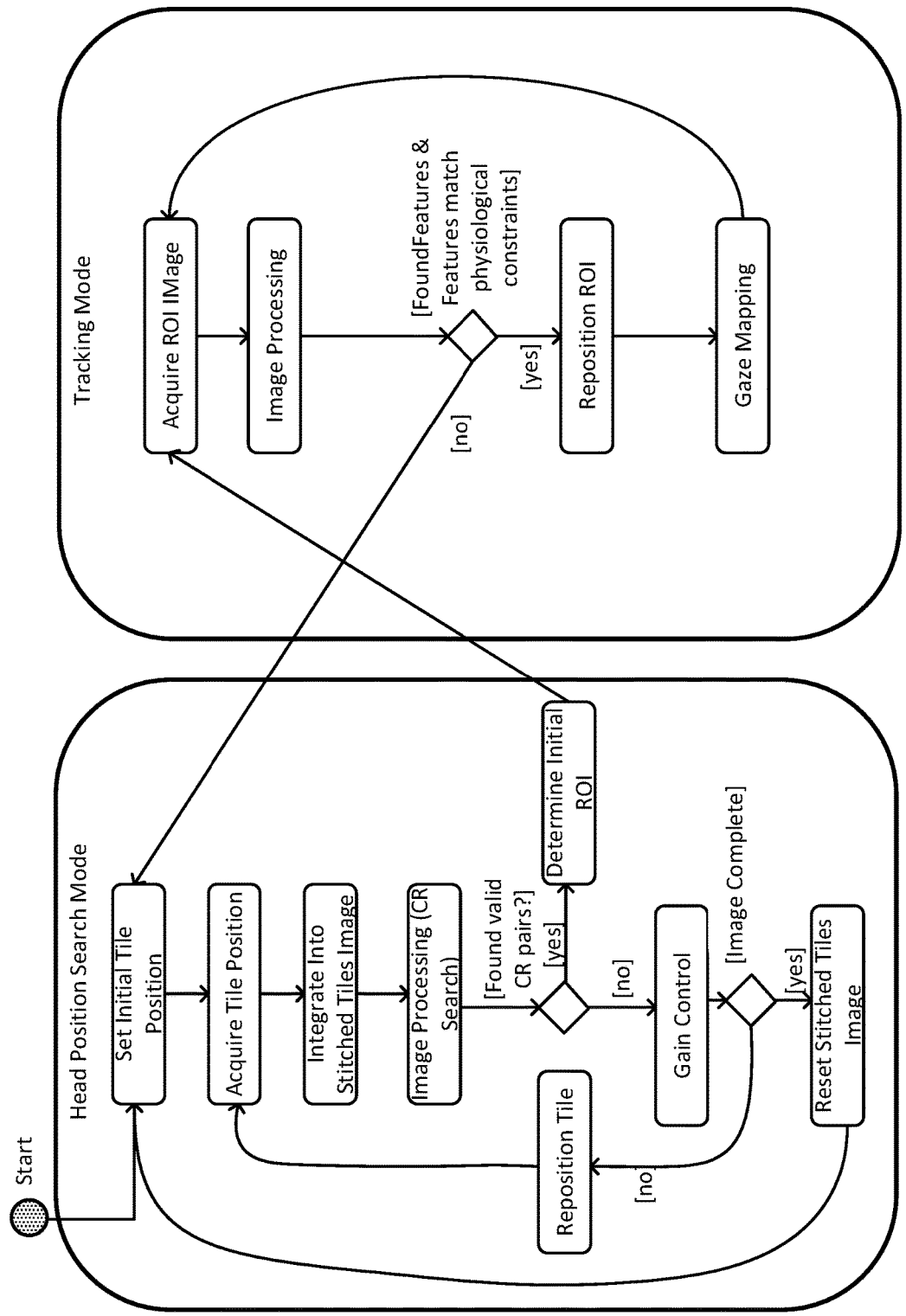
Figure 3: Scanning for Head Position Using Tile Stitching

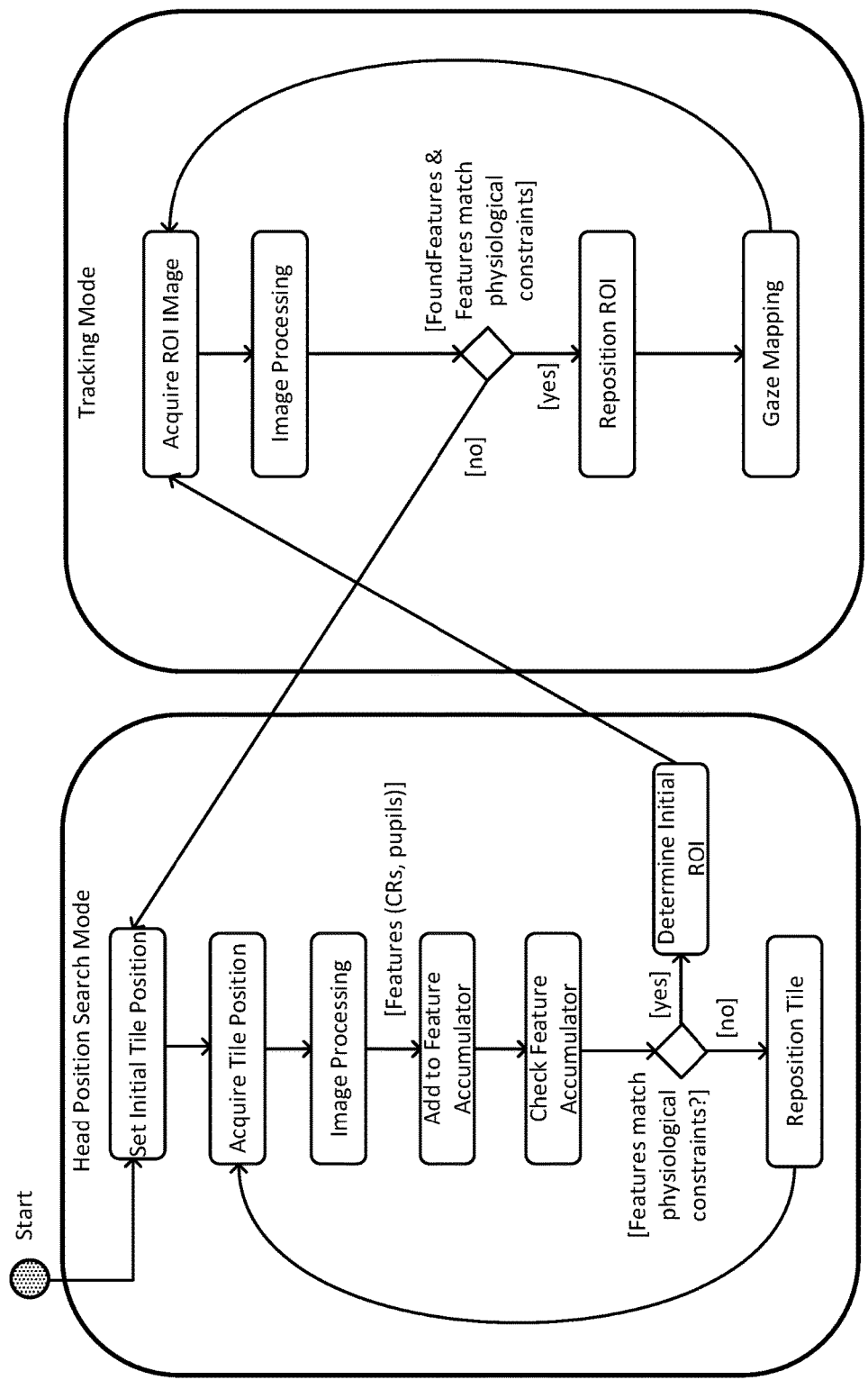
Figure 4: Scanning for Head Position using dedicated tiles

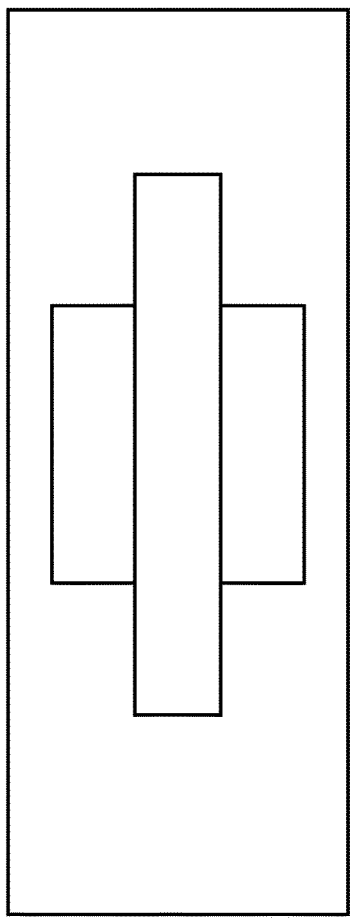
Figure 5: Different tile sizes
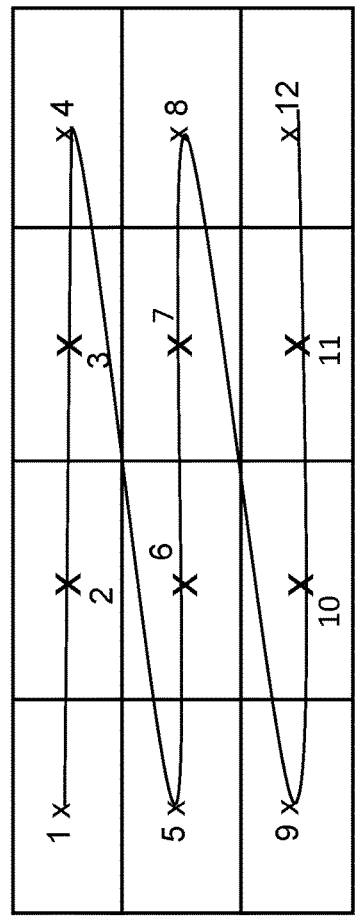
Figure 6: Linewise tile path

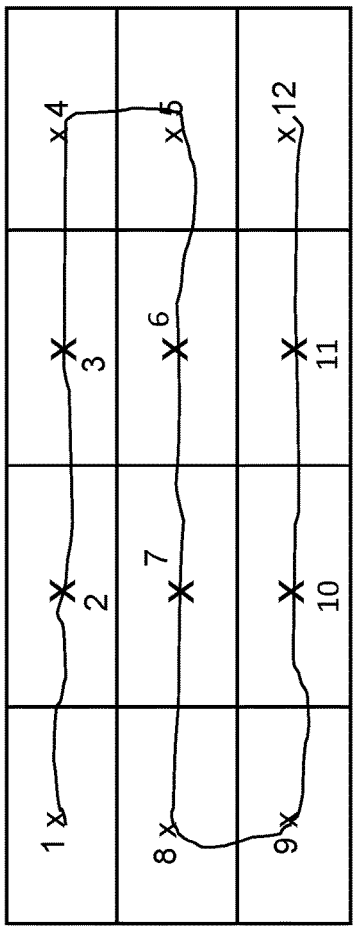
Figure 7: Linewise tile path, opposite direction
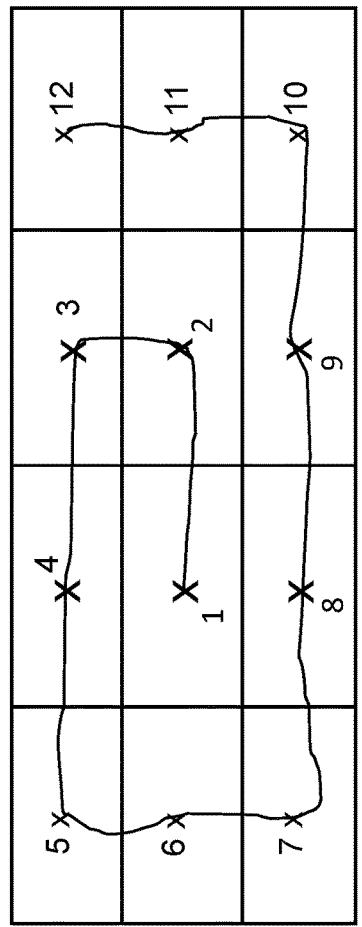
Figure 8: Spiral tile path

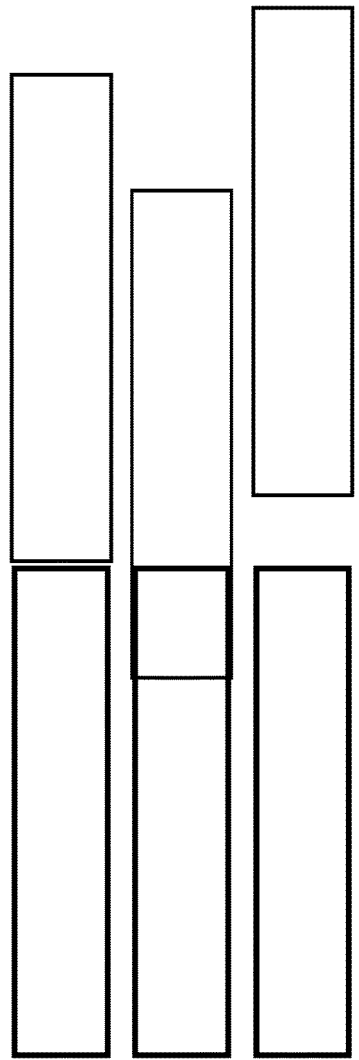
Figure 9: Radial tile
Figure 10: Tile edges: aligned, overlapping or with a gap

TILED IMAGE BASED SCANNING FOR HEAD POSITION FOR EYE AND GAZE TRACKING

RELATED APPLICATIONS

This Application is a continuation of U.S. patent application Ser. No. 14/428,621 ("the '621 application), filed Mar. 16, 2015, which is a national stage application of PCT/EP2013/070039 ("the '039 application), filed Sep. 26, 2013, which claims priority to EP 12186357.5 filed on Sep. 27, 2012 and to EP 12189825.8 filed on Oct. 24, 2012. The '621 and '039 applications are herein incorporated by reference.

FIELD OF THE INVENTION

This invention is concerned with eye gaze tracking, in particular with increasing the frame rate of camera based remote eye tracking systems using ROI based image acquisition and determining an initial ROI position for eye tracking.

BACKGROUND OF THE INVENTION

In current eye tracking systems camera images are processed to determine the position and/or gaze direction of an eye or the eyes. This can be done by detecting features in the image. Features are, for example, pupils and corneal reflexes.

For each feature, typically size, contour and position are extracted. Subsequent processing calculates gaze vector and gaze point from these features.

Camera based remote eye trackers provide a large working range for head movement. With a fixed focal length of the camera lens and without joints to change camera orientation, the working range has to be covered completely by the camera sensor.

Due to limited bandwidth of the camera bus, the frame rate of the system depends on size and spatial resolution of the grabbed image. Covering the full working range within a single image at full spatial resolution allows a minimal frame rate only, due to the large amount of data of full spatial resolution.

However, miscellaneous eye tracking applications require high sampling rates that cannot be provided using permanent full spatial resolution image acquisition.

This problem is addressed with ROI (region of interest) based image acquisition which allows higher frame rates compared to full spatial resolution image acquisition because the ROI covers a fractional part of the sensor only. The ROI size is set in a way that the ROI image covers all features needed for eye tracking and the sampling rate during ROI image acquisition fulfils the system requirements regarding temporal resolution.

Patent EP 1 562 469 B1 describes a solution that uses full frame based image acquisition to initially detect the position of the eye or eyes on the camera sensor. It then creates an ROI around the eye or eyes to track the eye within this region only. This results in reduced bandwidth requirements and can thus be used to increase camera readout frame rate. However, this speed-up does not apply to the initial read out of the full frame. Therefore, the minimum time that is required to find the eyes is determined largely by the time it takes to read out the full frame.

To find the initial ROI position, a system starts in Head Position Search Mode, wherein generally a full spatial resolution based image acquisition is used. "Head Position Search Mode" refers to a mode in which the acquired image is searched for one or more features which represent the eyes or are indicative of the head position or the eye position. As soon as the head or the eyes are detected, the system continues acquiring ROI images of an ROI around the eye or eyes. ROI gets positioned where it covers the detected eye or eyes.

The system then continues in Tracking Mode wherein features are extracted from the ROI image and used for further processing. The ROI position is moved according to head movements, depending on feature positions. If tracking of visible eye features fails, the system returns to the head position search mode.

However, various problems continue to exist. Using full spatial resolution based image acquisition for head position search forces the system to operate temporarily at a lower frame rate than required by the system. On the other hand, such a low full-frame speed of the camera determines the time between the subject being in front of system (ready to track) and the actual start of the tracking. Increasing this pick-up speed and reducing the system latency is highly desirable.

Moreover, switching between full spatial resolution based image acquisition and ROI based image acquisition causes a delay in camera operation with many common camera models which results in a decreased data rate.

A final issue is that changes in data frame rate complicate the subsequent data analysis due to frame rate dependent parameters.

It is therefore an object of the present invention to avoid these problems related to full spatial resolution based image acquisition, and in particular to reduce the time to find the initial ROI position.

SUMMARY OF THE INVENTION

Some embodiments may be summarized such that there is an initial head position or eye position search mode, in which the ROI is determined which is to be used for the subsequent tracking mode. In this head or eye position search mode initially only a part of the image sensor is read out and searched for one or more features to detect eye or head position. If the search is successful, the tracking ROI is determined based on said features or other means of image analysis or modeling. If not, then a further portion of the sensor is read out. This can be done by shifting the read out area or areas of the image sensor. Then the newly read out area(s) may be searched and analyzed separately. Also the two portions may be stitched to search a combined or stitched tile image. These steps of reading out further parts and searching for features may be repeated until the ROI to be used for the tracking mode can be determined. In none of the steps a full frame is read out, but always only a portion of the full sensor area.

According to one embodiment, there is provided an eye tracking method comprising:
  capturing image data by an image sensor;
  determining a region of interest as a subarea or disconnected subareas of said sensor which is to be read out from said sensor to perform an eye tracking based on the read out image data;
  wherein said determining said region of interest comprises:
    a) initially reading out only a part of the area of said sensor;

b) searching the image data of said initially read out part for one or more features representing the eye position and/or the head position of a subject to be tracked;

c) if said search for one or more features has been successful, determining the region of interest based on the location of the successfully searched one or more features, and d) if said search for one or more features has not been successful, reading out a further part of said sensor to perform a search for one or more features representing the eye position and/or the head position based on said further part.

This enables a faster determination of the region of interest (ROI) for the actual eye or gaze tracking because initially only a part of the sensor area is read out, in contrast to reading out a full frame according to the prior art. Thus, the system does not need to operate with lower frame rates. Rather, the system can operate at a constant frame rate and pick-up speed is increased.

According to one embodiment, said steps of searching for one or more features and determining said region of interest based on the location of the found features or reading out further data, are iteratively repeated until the location of said one or more features is successfully searched and the region of interest can be determined.

This iterative search for the features representing the eye position and/or the head position in small parts of the image is much more efficient than a corresponding search on a full frame image.

According to one embodiment, said read out parts of sensor data are tiled to a combined image based on which the search for one or more features is performed.

Tiling the read out parts of the image to a combined image improves the chances for detecting a feature which could not be detected in a previous combined image or part of the image.

According to one embodiment, the method further comprises storing the successfully searched one or more features in a feature accumulator, analyzing the features stored in the feature accumulator; and determining the region of interest based on the analyzed features.

The feature accumulator enables an analysis of accumulated features, such as applying constraints or knowledge to eliminate false positively detected features.

According to one embodiment, said analyzing the features stored in the feature accumulator involves time of detection of a feature.

The time of detection of a feature enables tracking of head movements and assigning confidence values to features to privilege newer features compared to older features from the same area.

According to one embodiment, the method further comprises performing an eye tracking based on repeatedly reading out the determined region of interest from said sensor and determining one or more features therein, wherein preferably the location of said region of interest is adapted based on the location of the determined features.

Once the features representing the eye position and/or the head position are found, the region of interest can be determined and provides the most promising starting point for tracking the eyes and/or the head.

According to one embodiment, said initially reading out only a part of said sensor is based on the last region of interest which has been used for tracking.

This may be a "good guess" of the initial subarea, especially if the tracking has been lost e.g. due to image distortions or blinking without the head of the subject having been moved. Then there is a relatively high likelihood that the initially read out subarea contains or is located close to the area where the searched features are located.

According to one embodiment, said initially reading out only a part of the area of said sensor is performed when (or even despite) there is no information on the one or more features representing the eye position and/or the head position of a subject to be tracked.

The initial read-out of only a part of the image enables a significant reduction of the time between the subject being in front of system (ready to track) and the actual start if the tracking. This approach is in contrast to the prior art which reads out a whole image when there is no information on features in the image available, and which is based on the prior art paradigm requiring that the whole image has to be read out in order to catch any possible feature location.

According to one embodiment, said initially reading out only a part of the area of said sensor is based on a previous valid head position, an external input that provides information about head position, or a probability density function describing head position likelihoods that are supplied a priori or are created during tracking the current subject or subjects.

According to one embodiment, said reading out a further part of said sensor comprises selecting a further part depending on statistics that determine the further part with the highest probability of covering the user's head.

In this way, there are better chances for detecting features than with a purely random selection of a further part.

According to one embodiment, said reading out a further part of said sensor comprises selecting a further part row by row, line by line, or in a spiral around a center.

According to one embodiment, said searching the image data comprises searching the image data of said initially read out part for one or more features representing the eye position and/or the head position of multiple subjects to be tracked.

According to one embodiment, reading out a further part of said sensor comprises changing the size of the further part, compared to the previously read out part.

According to one embodiment, said searching the image data comprises using horizontal or vertical or combined horizontal and vertical binning, skipping, or sub-sampling of the image data of said initially read out part to accelerate search.

According to one embodiment, a system for eye tracking comprises:
  an image sensor for capturing image data;
  a module for determining a region of interest as a subarea of said sensor which is to be read out from said sensor to perform an eye tracking based on the read out image data;
  wherein said module for determining said region of interest further comprises:
    a) a module for initially reading out only a part of the area of said sensor;
    b) a module for searching the image data of said initially read out part for one or more features representing the eye position and/or the head position of a subject to be tracked;
    c) a module for determining the region of interest based on the location of the successfully searched one or more features, if said search for one or more features has been successful, and
    d) a module for reading out a further part of said sensor to perform a search for one or more features representing the eye position and/or the head position based on said further part, if said search for one or more features has not been successful.

According to one embodiment, the system for eye tracking comprises one or more modules for performing a method according to one of the previously defined embodiments of the invention.

According to one embodiment, there is provided a computer program which, when being executed on a computer, enables said computer to carry out a method according to one of the embodiments of the invention.

DESCRIPTION OF THE DRAWINGS

FIG. 1 schematically illustrates a sensor area split into tiles.

FIG. 2 schematically illustrates head position search mode and tracking mode.

FIG. 3 schematically illustrates a method for scanning for head position using tile stitching.

FIG. 4 schematically illustrates a method for scanning for head position using dedicated tiles.

FIG. 5 schematically illustrates different tile sizes.

FIG. 6 schematically illustrates a line wise tile path.

FIG. 7 schematically illustrates a line wise tile Path in opposite direction to FIG. 6.

FIG. 8 schematically illustrates a spiral tile path.

FIG. 9 schematically illustrates a radial tile path.

FIG. 10 schematically illustrates tile edges: aligned, overlapping, or with a gap.

DETAILED DESCRIPTION

In the following embodiments of the invention will be described in somewhat more detail. The embodiments for eye or gaze tracking described in the following can be used for just the purpose of determining and tracking the eye position or the gaze itself, or they may be applied in various fields such as marketing research, psychology, medical applications including surgery, control applications, simulators and generally as a part of human-machine-interfaces.

The system starts in Head Position Search Mode. The goal of this mode is to determine an initial ROI position that can be used in subsequent Tracking Mode. This transition can be realized as soon as there are enough features detected that allow the system to determine the head or eye position and derived from the head or eye position the initial position of the ROI for Tracking Mode.

Scanning for Head Position Using Tile Stitching

A system for eye or gaze tracking according to one embodiment starts in Head Position Search Mode. The goal of this mode is to find an initial region of interest (ROI) position that can be used in subsequent Tracking Mode. In Head Position Search Mode, the system searches for eyes, pupils, corneal reflexes, or any other features of the eye or the head which are useful for determining the position of the eye or the head and to identify or determine based thereon an initial ROI position to be used in the subsequent Tracking Mode. In this regard reference is made to FIG. 1 which is a schematic illustration showing a sensor area 10 split into parts or tiles 11.

In Head Position Search Mode, the system uses ROI based image acquisition, in which a part or tile 11 of the sensor area 10 is read out. A part or tile of the sensor area will be designated as a tile in the following.

Reading out only tile of the image area is in contrast to the prior art which reads out a whole image when there is no information on features in the image available, and which is based on the prior art paradigm requiring that the whole image has to be read out in order to catch any possible feature location.

The position of tile 11 is changed from one acquisition step to the next. One way of doing this may be to have consecutive tiles 11 adjacent to one another. Different options for read-in sequences of tiles 11 will be described below in connection with FIGS. 6 to 9. Tiles 11 are aggregated to a stitched tile image. The stitched tile image may also be referred to as a combined image. During each step, features needed for eye tracking or head tracking are extracted from the stitched tile image. As soon as the features match with physiological constraints, e.g. the shape of the pupil if the searched feature is the pupil, the initial ROI position is found and the system switches to Tracking Mode.

In this regard reference is further made to FIG. 2 which shows Head Position Search Mode and Tracking Mode. In Head Position Search Mode, a new tile is read in and aggregated with the present stitched tile image which is then analyzed for features. If the feature search is successful, the initial ROI image is determined from the present stitched tile image and Tracking Mode is entered, else the method returns to the initial step.

The determination of the ROI for the Tracking Mode may e.g. just consist in using the tiled image as ROI for the tracking. Alternatively the position of the found features representing the eye position may be used to determine an ROI according to a certain scheme around the eye position, e.g. by choosing a square or a rectangle of a predetermined size around the position of the eye as determined by the features.

In Tracking Mode the ROI image is analyzed for the required features. If the required features have been found, the ROI image is repositioned; else Head Position Search Mode is entered again.

Further reference is made to FIG. 3 which shows scanning for head position using tile stitching. In the first step of Head Position Search Mode, a tile position is initialized. The tile is then acquired, integrated into the present stitched tiles image, and image processing is performed. If the required features are found, Tracking Mode is entered with an ROI image determined from the stitched tiles image. Else, image parameters may be adapted (e.g., gain control). If the whole image has been processed, the stitched tiles image is reset and the procedure is restarted, else the tile is repositioned and the second step in which a tile is acquired is re-entered.

Alternatively, instead of resetting the whole stitched tiles image corresponding to the whole sensor area, the stitched tile image is not reset and new tiles are iteratively read out from the image sensor, replacing the corresponding tiles in the stitched tiles image.

In Tracking Mode, the ROI image (initially determined from the stitched tiles image) is acquired and processed. If the found features match the physiological constraints, tracking is continued and the ROI is repositioned, else Head Position Search Mode is re-entered. Finally, gaze parameters such as gaze vector and gaze point are determined.

Scanning for Head Position Using Dedicated Tiles

As an alternative to the previously described scanning for head position using tile stitching described with reference to FIG. 3, FIG. 4 shows scanning for head position using dedicated tiles.

In Head Position Search Mode, the system uses ROI based image acquisition, as in scanning for head position using tile stitching, in which a part or tile 11 of the sensor area 10 (cf. FIG. 1) is read out. The tile position is changed for each acquisition step.

The tile placement may be too small for a single tile to contain all features corresponding to a head and/or an eye or a pair of eyes. Therefore, features are extracted from a tile and stored in a feature accumulator as feature candidates. The feature accumulator will be described in the following. It is therefore not necessary to maintain the previously visited tiles in a stitched tiles image. Image processing therefore operates on a smaller image region which reduces the processing effort.

After adding features to the feature accumulator, all accumulated feature candidates are checked for matching with physiological constraints. Such physiological constraints may be e.g. the distance between two found eyes as represented by features, the size and shape of a pupil, the location of features, or their parts being found in neighboring tiles, e.g. half of a pupil being found in one tile and the other one in the neighboring tile, etc. As soon as the features match with the constraints, the initial ROI can be determined and the system switches to Tracking Mode. The tracking operates as described with respect to scanning for head position using tile stitching in FIG. 3.

In an alternative embodiment (not illustrated), scanning for head position is performed by using both tile stitching as in FIG. 3 and dedicated tiles as in FIG. 4. This approach may combine the advantage of reduced processing effort of the dedicated tiles approach with the possibility to search again for a missing feature on an extended tiles image.

Feature Accumulator

The feature accumulator according to one embodiment is a database that contains geometrical properties like size and position of the features that are extracted from image processing for each dedicated tile. Additional information like time of exposure, confidence and tile properties are attached to each feature dataset. Goals of the feature accumulator are for example:

Analyze accumulated features to the end to switch to tracking mode and to determine initial ROI position for Tracking Mode Selection of subsequent tile to continue in Head Position Search Mode To detect head position, accumulated features are checked for geometrical and physiological constraints, e.g. by using one or more of the following:

Ray path of illumination is calculated from a physiological model of the eye and geometrical setup of camera and illumination diodes. From that, constraints for position of corneal reflexes and pupils can be derived and applied to the accumulated features.

Knowledge of head movement speed is used to exclude false positively detected features dependent from spatial and temporal distance to the last known position of that feature.

Binocular eye distance is used to exclude false positively detected features depending on the ranges for the distances between features of left and right eye.

As soon as the system detects reasonable features, the system switches to tracking mode. The initial ROI for tracking mode is defined in a way that it includes the accepted features.

The feature accumulator can be applied both in scanning for head position using tile stitching and in scanning for head position using dedicated tiles.

Tile Sizes

FIG. 5 shows different tile sizes which are preferably applied for dedicated tiles (FIG. 4) but which can also be used with tile stitching (FIG. 3). As illustrated in FIG. 5, tile sizes can be:

constant not constant (e.g. to cover larger horizontal or vertical areas by merging two adjacent tiles that would have been grabbed consecutively)

Initial Tile Positioning

According to embodiments, there are different ways of instantiation of search in Head Position Search Mode which can be applied both for tile stitching (FIG. 3) and dedicated tiles (FIG. 4):

Static: start in the middle or start where there is a high probability of finding the head position immediately Based on last tracking position Based on external information (e.g., based on web cam face detection result) which can be used for an approximation of the eye position Tile Paths FIGS. 6 to 9 show different paths for consecutively read in tiles according to embodiments during Head Position Search Mode which can be applied both for tile stitching (FIG. 3) and dedicated tiles (FIG. 4).

The order of subsequently grabbed tiles affect the time until the head position is found The order for subsequently grabbing tiles may be as follows or in other suitable patterns.

Easiest: row by row, line by line

Spiral around center

Spiral around last tracked position

Radial around center

Radial around last tracked position

Sampling based on probability density function

Random or pseudo-random

Tile Edges

In Head Position Search Mode which can be applied both for tile stitching (FIG. 3) and dedicated tiles (FIG. 4), tiles are defined in a way that their borders are overlapping or aligned or there is a gap between tiles.

Using overlapping edges simplifies detection of features close to the ROI border. Thus, complications with areas covered by features subdivided by ROI borders are avoided. FIG. 9 shows tile edges (from bottom to top): aligned, overlapping or with a gap.

Tracking Mode

As soon as head position search succeeds and the ROI for tracking has been determined, the system switches to Tracking Mode.

According to one embodiment, while the system remains in Tracking Mode, it creates statistics for a start tile for tile stitching (FIG. 3) or for dedicated tiles (FIG. 4) in a way that the tile with the highest probability for finding the head position can be used first in Head Position Search Mode.

Tracking ROI is moved according to head position movement. When system fails to detect the required features within the ROI, it switches back to Head Position Search Mode.

Using Multiple ROIs to Track Multiple Users

According to one embodiment, the Head Position Search Mode is modified in a way that it scans the tracking volume for multiple users. For that, the Head Position Search Mode calculates multiple tiles around all features that match physiological and geometrical constraints. One initial tile position is generated for each subject.

The tracking mode is modified in a way that multiple ROIs passed from Head Position Search Mode are handled, one for each subject. Each ROI is moved according to the subject's head movements.

If there are no eye features available in one ROI, the system stops pursuing that specific subject's head movement. As long as there are ROIs available that contain eye features, the system does not switch back to Head Position Search Mode.

The system switches back to head position search mode if there aren't any ROIs left that contain eye features.

According to one embodiment, while in Tracking Mode, the system scans the area outside the tracking ROI permanently for additional users. This is realized equivalently to Head Position Search Mode. That means, for multiple user tracking, the system is running in Head Position Search Mode and in Tracking Mode simultaneously.

Using Multiple ROIs to Increase Sampling Rate

To increase sampling frequency and/or reduce bandwidth in Tracking Mode, according to one embodiment, multiple smaller ROIs can be used in place of a larger one, placing and sizing the ROIs to suit the detection of features required for the task. For example, one small ROI can be centered on each eye instead of a single ROI for both eyes. The summed area of the two ROIs is smaller than the area of the large ROI. This is realized by not grabbing the area where the nose bridge is expected. Decreasing the grabbed area size increases sampling frame rate.

Resolution Reduction

Binning, (row and/or column) skipping, or sub-sampling can be used to decrease the spatial resolution and to increase the frame rate. Using such means of resolution reduction in Head Position Search Mode allows (compared to full resolution sensor readout):

By using larger tiles with the same sampling frequency, a larger sensor area is covered. This increases the probability of finding features.

When using the same tile size with faster sampling frequency, head position related features can be detected earlier and the system can switch faster to Tracking Mode.

Binning

Adding the signal of adjacent pixels in the image sensor reduces the image processing effort since the number of processed pixels is reduced. Adjacency can be horizontal, vertical, or both, and any number of adjacent pixels can be added or their signal combined, but typical modes include 2×1 (2 pixel adjacent horizontally), 1×2 (2 adjacent vertically), 2×2 (4 pixels adjacent horizontally, vertically and diagonally), 4×1, 1×4, 4×4, etc.

Binning can be done on the sensor level, on the analog or digital output of each pixel, or done digitally in software or by a device driver.

Skipping

Partial readout where pixels outputs are not read, not transmitted or are just ignored according to a certain spatial recurring pattern, for example by but not limited to skipping every. other pixel vertically, horizontally, or both.

This can be performed on the sensor level, in software, or both.

Sub-sampling is similar to binning, but the signals are not added, instead they are combined according to a filtering function; in the simplest case, such filtering function consists in averaging the output of all the pixels contained within the sub-sampling adjacency pattern.

More complex patterns include bicubic interpolation, Lanczos interpolation, etc.

Adjacency patterns are similar to the patterns used for binning, i.e. 2×1, 1×2, 2×2, 4×4, etc. Sub-sampling can be performed digitally or analog on the sensor level, or digitally in software, or both.

In the following, some embodiments are described.

1) A system, comprising:
   a) one or more image sensor(s) or arrays of light sensitive elements able to capture images; a processing unit or CPU which receives and processes images captured by said arrays of light sensitive elements;
   b) a method for determining one or more parameters of one or more user(s) eye(s), by means of processing images acquired with said system, identifying and detecting one or more features of a user's eyes, such as but not limited to a pupil, a cornea, and iris, a sclera, a limbus, a retina, blood vessels, a reflection of a light source;
   c) a model of the user's eye and eye tracking system, which is used to correlate said feature (a) detected in said image (o) with actual position(s), orientation(s) and dimensions of the user's eyes in a chosen reference coordinate system;
   d) a search method for determining the position of one or more user(s) eye(s) while at any given sampling interval using only a partial readout of said image sensor(s) or arrays of light sensitive elements; where a partial readout consists of reading or collecting the output of only a subset of the light sensitive elements or subregion or subregions of the array/image sensor (Region Of Interest or ROI)

2) The embodiment 1), which may or may not include one or more light emitting elements 3) The embodiment 1-2 where some form of resolution reduction, such as binning or skipping or sub-sampling may or may not be used according to a horizontal or vertical or combined horizontal and vertical pattern to selectively reduce the number of pixels being transmitted or processed 4) The embodiment 1-3, where the search method tries to substantially locate or identify at least part of at least one said feature within the (sub)set of light sensitive element or ROI defined by a partial readout occurred within a given sampling interval 5) The embodiment 1-4, where the size and shape of the ROI can be set to constant values 6) The embodiment 1-5, where the size and shape of the ROI can be dynamically changed at different time periods 7) The embodiments 1-6, where the searching method consists in stitching or combining within a processing unit's memory one or more of said partial readouts captured at different sampling intervals, to form a larger (sub)set of an image sensor's light sensitive elements to be processed to substantially locate or identify at least part of at least one said feature as in embodiment 4

8) The embodiments 1-6, where the features or parts thereof located within an ROI can be stored within a Feature Accumulator or storage space within a computing unit, together with said features' related properties which may include: feature's position, size, (partial) shape, time of detection; ROI frame size and position 9) The embodiment 8, where physiological and geometrical constraints are applied to features stored in the Feature Accumulator to exclude false positive detections, to reconstruct a feature's complete shape from one or more partial fragments, and to use said together with said model to substantially determine a user's head position and/or orientation and/or one or more eyes position(s) and/or orientations 10) The embodiment 9, where time of detection of one or more said features can be used to determine a confidence value to features which may be used to privilege newer features compared to older features from the same area or ROI 11) The previous embodiments, where time of detection of features can be used to determine movement velocity of one or more heads or one or more eyes and said velocity(ies) can be used to track and/or predict head(s) and eye(s) positions at future time intervals, where said prediction can be used to determine future location(s) of said ROI(s)

12) The previous embodiments, where the position of one or more ROIs can be defined statically:
   a) In the middle of the sensor
   b) At a corner of the sensor
   c) At a position with a high probability of finding the head position. Probability depends on head position statistics that has been created offline.

13) The previous embodiments, where the position of one or more ROIs can be defined dynamically:
   a) Based on last valid head position
   b) Based on external input that provides information about head position
   c) Based on probability density function created during tracking the current subject or subjects 14) The previous embodiments, where the path of movement of one or more ROIs in subsequent time intervals substantially depends on statistics that determine the dedicated positions with the highest probability of finding user's head(s), eye(s) and features thereof 15) The embodiment 14, where said path of movement substantially follows a spiral path 16) The embodiment 14, where said path of movement substantially follows a radial path 17) The method in claim 14, where said path of movement substantially follows a systematic row by row or column by column path 18) The embodiment 14, where said path of movement substantially follows a random or pseudo-random path 19) The previous embodiments, where the ROI positions assumed at subsequent time intervals may or may not overlap 20) The previous embodiments, where the ROI positions assumed at subsequent time intervals may or may not have aligned edges to minimize the overall sensor readout area 21) The previous embodiments, where multiple ROIs are specifically created and used to detect and track simultaneously one or more eyes for more than one user 22) The previous embodiments where ROIs are moved according to the corresponding subject's head movement.

23) The previous embodiments where ROIs are moved in a way to predict and track each user's head and eye movement as to being able to detect in subsequent frames one or more features which are used to identify one or more user(s) eye(s)

24) The previous embodiments where ROIs are positioned or moved in a way to search and detect potential new users or temporarily lost users 25) The previous embodiments, where multiple ROIs are used to substantially reduce sensor area read out in comparison to a single ROI by being centered close to the expected location of a user(s)' eyes.

26) The embodiment 25, where one ROI is positioned in proximity of the center of a user's left eye, one ROI is positioned in proximity of the center of a user's right eye and the area where the nose bridge of the user is expected to be is not read out.

The invention claimed is:

1. An eye tracking method comprising:
   capturing image data by an image sensor;
   determining a region of interest as a subarea or disconnected subareas of said image sensor which is to be read out from said image sensor to perform an eye tracking based on the read out image data;
   wherein said determining of said region of interest comprises:
   a) initially reading out only a part of the area of said image sensor;
   b) searching the image data of said initially read out part for one or more features representing eye and/or head position of a subject to be tracked;
   c) if said search for one or more features has been successful, determining the region of interest based on the location of the successfully searched one or more features, and
   d) if said search for one or more features has not been successful, reading out a further part of the area of said image sensor to perform a search for one or more features representing the eye position and/or the head position based on said further part, wherein the further part is different from the initially read out part.

2. The eye tracking method of claim 1, wherein said steps of searching for one or more features and determining said region of interest based on the location of the found features or reading out further image sensor data, are iteratively repeated until the location of said one or more features is successfully found and the region of interest can be determined.

3. The eye tracking method of claim 2 wherein said read out parts of said image sensor data are tiled to a combined image based on which the search for one or more features is performed.

4. The eye tracking method of claim 2, further comprising:
   storing the successfully searched one or more features in a feature accumulator;
   analyzing the features stored in the feature accumulator; and
   determining the region of interest based on the analyzed features.

5. The eye tracking method of claim 4, wherein said analyzing the features stored in the feature accumulator involves time of detection of a feature.

6. The eye tracking method of claim 2, further comprising:
   performing an eye tracking based on repeatedly reading out the determined region of interest from said image sensor and determining one or more features therein, wherein preferably the location of said region of interest is adapted based on the location of the determined features.

7. The eye tracking method of claim 2, wherein said initially reading out only a part of said image sensor is based on the last region of interest which has been used for tracking.

8. The eye tracking method of claim 1, wherein said initially reading out only a part of the area of said image sensor is performed when there is no information on the one or more features representing the eye position and/or the head position of a subject to be tracked.

9. The eye tracking method of claim 2, wherein said initially reading out only a part of the area of said image sensor is based on a previous valid head position, an external input that provides information about head position, or a probability density function describing head position likelihoods that are supplied a priori or are created during tracking the current subject or subjects.

10. The eye tracking method of claim 2, wherein said reading out a further part of said image sensor comprises selecting a further part depending on statistics that determine the further part with the highest probability of covering the user's head.

11. The eye tracking method of claim 2, wherein said reading out a further part of said image sensor comprises selecting a further part row by row, line by line, randomly, pseudo-randomly, radially around a center, or in a spiral around a center.

12. The eye tracking method of claim 2, wherein said searching the image data comprises searching the image data of said initially read out part for one or more features representing the eye position and/or the head position of multiple subjects to be tracked.

13. The eye tracking method of claim 2, wherein said reading out a further part of said image sensor comprises changing the size of the further part, compared to the previously read out part.

14. The eye tracking method of claim 2, wherein said searching the image data comprises using horizontal or vertical or combined horizontal and vertical binning, skipping, or sub-sampling of the image data of said initially and further read out to accelerate search.

15. A system for eye tracking comprising:

an image sensor for capturing image data;

a module for determining a region of interest as a subarea or disconnected subareas of said image sensor which is to be read out from said image sensor to perform an eye tracking based on the read out image data;

wherein said module for determining said region of interest further comprises:
   a) a module for initially reading out only a part of the area of said image sensor;
   b) a module for searching the image data of said initially read out part for one or more features representing eye and/or head position position of a subject to be tracked;
   c) a module for determining the region of interest based on the location of the successfully searched one or more features, if said search for one or more features has been successful; and
   d) a module for reading out a further part of the area of said image sensor to perform a search for one or more features representing the eye position and/or the head position based on said further part, if said search for one or more features has not been successful, wherein said further part is different from the initially read out part.

* * * * *